(12) United States Patent
Sokulin et al.

(10) Patent No.: US 11,109,841 B2
(45) Date of Patent: Sep. 7, 2021

(54) METHOD AND SYSTEM FOR SIMULTANEOUSLY PRESENTING DOPPLER SIGNALS OF A MULTI-GATED DOPPLER SIGNAL CORRESPONDING WITH DIFFERENT ANATOMICAL STRUCTURES

(71) Applicant: General Electric Company, Schenectady, NY (US)

(72) Inventors: Alexander Sokulin, Tirat Carmel (IL); Menachem Halmann, Wauwatosa, WI (US); Cynthia A. Owen, Powhatan, AR (US); Dani Pinkovich, Tirat Carmel (IL)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 351 days.

(21) Appl. No.: 16/211,697

(22) Filed: Dec. 6, 2018

(65) Prior Publication Data
US 2020/0178935 A1 Jun. 11, 2020

(51) Int. Cl.
*A61B 8/08* (2006.01)
*A61B 8/02* (2006.01)
(Continued)

(52) U.S. Cl.
CPC ............. *A61B 8/488* (2013.01); *A61B 8/02* (2013.01); *A61B 8/463* (2013.01); *A61B 8/469* (2013.01);
(Continued)

(58) Field of Classification Search
CPC combination set(s) only.
See application file for complete search history.

(56) References Cited

U.S. PATENT DOCUMENTS 9,060,669 B1 * 6/2015 Mo .......................... A61B 8/08
2001/0016686 A1 * 8/2001 Okada ...................... A61B 8/13
600/454

(Continued)

FOREIGN PATENT DOCUMENTS

JP 2012135523 A * 7/2012
JP 2012135523 A 7/2012
(Continued)

OTHER PUBLICATIONS

JP2012135523 Thomson Native Machine Translation, 20 pages.
(Continued)

*Primary Examiner* — Vikkram Bali
(74) *Attorney, Agent, or Firm* — McAndrews, Held & Malloy, Ltd.; Jacob Groethe; David Bates

(57) ABSTRACT

A system and method for simultaneously presenting Doppler signals of a Multi-Gated Doppler (MGD) signal corresponding to different anatomical structures is provided. The method includes receiving an MGD signal having a plurality of Doppler signals. The method includes analyzing the MGD signal to select multiple gates, each of the gates corresponding with a Doppler signal, and each of the selected gates associated with a different anatomical structure. The method includes selecting a set of parameters for each of the selected gates and applying each selected set of parameters for each of the selected gates. The selected set of parameters for each of the selected gates may be one or both of image acquisition parameters or display processing parameters. The method includes simultaneously presenting the Doppler signal for each of the selected gates at a display system after the each selected set of parameters is applied.

20 Claims, 5 Drawing Sheets

(51) Int. Cl.
  *A61B 8/00* (2006.01)
  *A61B 8/06* (2006.01)
  *G01S 15/89* (2006.01)

(52) U.S. Cl.
  CPC .......... *A61B 8/5223* (2013.01); *A61B 8/5292* (2013.01); *A61B 8/065* (2013.01); *A61B 8/0883* (2013.01); *A61B 8/4444* (2013.01); *G01S 15/8979* (2013.01)

(56) References Cited

U.S. PATENT DOCUMENTS

2009/0105594 A1* 4/2009 Reynolds ................ A61B 8/06
                                                              600/454
2017/0086780 A1   3/2017 Sokulin et al.

FOREIGN PATENT DOCUMENTS

| JP | 201468980 A | | 4/2014 |
| JP | 2014068980 A | * | 4/2014 |
| WO | 2014119540 A1 | | 8/2014 |
| WO | WO-2019155226 A1 | * | 8/2019 ............... A61B 8/06 |

OTHER PUBLICATIONS

JP2014068980 Thomson Native Machine Translation, 32 pages.
PCT application PCT/US2019/064818 filed Dec. 6, 2019—International Search Report/Written Opinion dated Mar. 17, 2020, 11 pages.
WO2014119540 EPO Machine Translation, 13 pages.

* cited by examiner

METHOD AND SYSTEM FOR SIMULTANEOUSLY PRESENTING DOPPLER SIGNALS OF A MULTI-GATED DOPPLER SIGNAL CORRESPONDING WITH DIFFERENT ANATOMICAL STRUCTURES

FIELD

Certain embodiments relate to ultrasound imaging. More specifically, certain embodiments relate to a method and system for simultaneously displaying at least two Doppler signals of a Multi-Gated Doppler (MGD) signal corresponding to different anatomical structures. In various embodiments, each of the Doppler signals corresponding to the different anatomical structures is acquired based on a different set of acquisition parameters and/or processed based on a different set of display processing parameters.

BACKGROUND

Ultrasound imaging is a medical imaging technique for imaging organs and soft tissues in a human body. Ultrasound imaging uses real time, non-invasive high frequency sound waves to produce a two-dimensional (2D) image and/or a three-dimensional (3D) image.

Pulsed-Wave (PW) and Continuous-Wave (CW) Doppler signals are rich signals that describe the spectrum of tissue and fluid velocities in a small volume from which the signals are acquired. During an ultrasound examination of a patient, it may be desirable to inspect the Doppler signal of multiple different anatomical structures, such as a mitral inflow signal and a tissue Doppler signal of a lateral basal point during a diastolic dysfunction examination. It may also be desirable for each of the Doppler signals corresponding to the different anatomical structures to be acquired and/or processed using different parameters The ultrasound operator performing the examination may attempt to collect the Doppler signals corresponding to each of the different anatomical structures consecutively, which is time consuming, requires special training and proficiency, and is subject to measurement variability that may affect the accuracy of the diagnosis. For example, the consecutive acquisition may lengthen the amount of time needed to obtain and process the Doppler signals of the multiple different anatomical structures. As another example, the consecutive acquisition may result in the Doppler signals of the multiple different anatomical structures being acquired during different heart cycles and/or different breathing cycles, which may reduce the accuracy of the diagnosis due to the variability of the measurements.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for simultaneously presenting Doppler signals of a Multi-Gated Doppler (MGD) signal corresponding to different anatomical structures, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Figure 1:
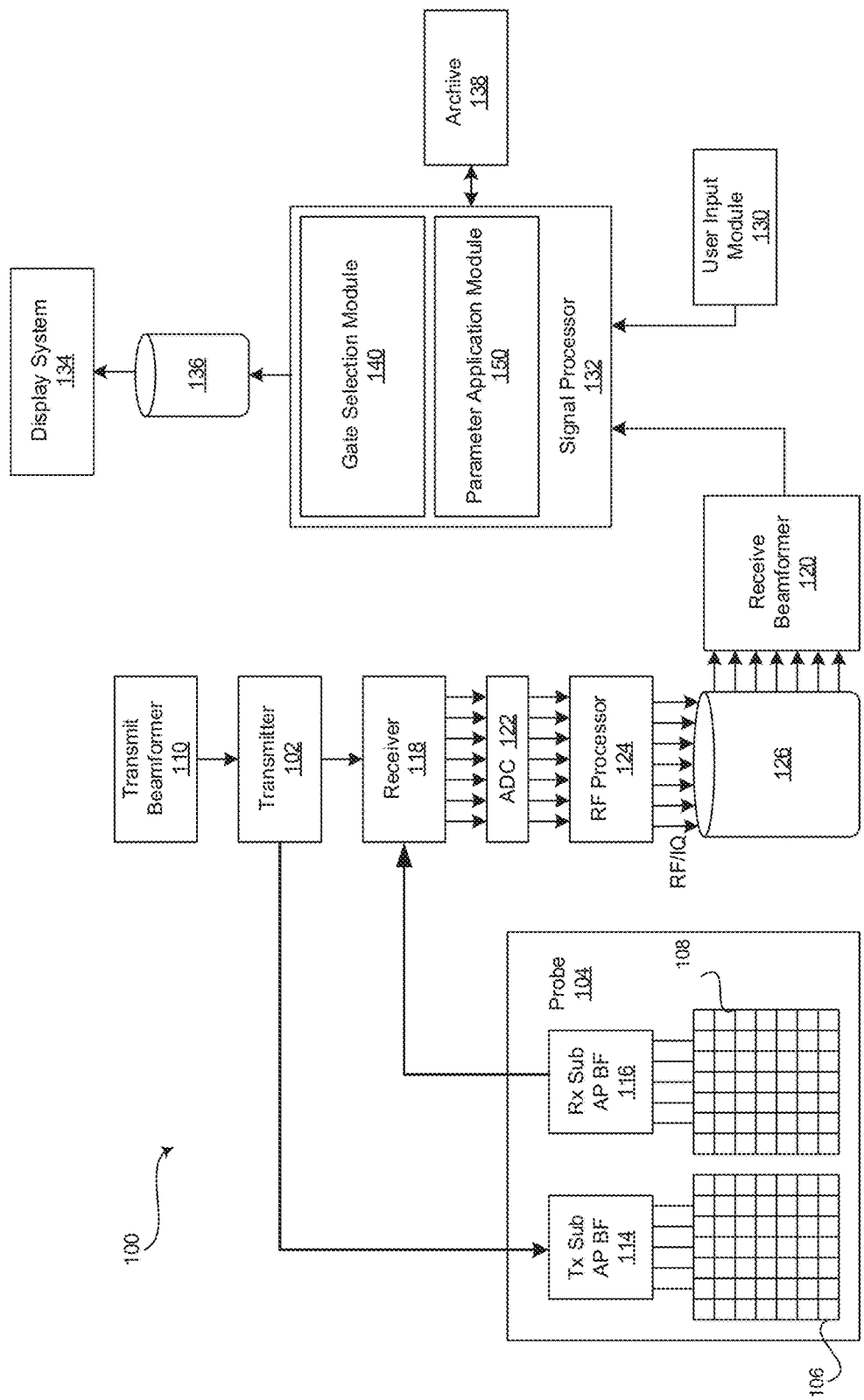
FIG. 1 is a block diagram of an exemplary ultrasound system that is operable to simultaneously present Doppler signals of a Multi-Gated Doppler (MGD) signal corresponding to different anatomical structures, in accordance with various embodiments.

Certain embodiments may be found in a method and system for simultaneously presenting Doppler signals of a Multi-Gated Doppler (MGD) signal corresponding to different anatomical structures. Various embodiments have the technical effect of providing enhanced visualization of multiple Doppler signals, each corresponding to a different anatomical structure. Moreover, certain embodiments have the technical effect of acquiring Doppler signals corresponding to different anatomical structures based on different acquisition parameters. Furthermore, aspects of the present disclosure have the technical effect of processing Doppler signals corresponding to different anatomical structures based on different display processing parameters.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), M-mode, three-dimensional (3D) mode, CF-mode, PW Doppler, CW Doppler, MGD, and/or sub-modes of B-mode and/or CF such as Shear Wave Elasticity Imaging (SWEI), TVI, Angio, B-flow, BMI, BMI_Angio, and in some cases also MM, CM, TVD where the "image" and/or "plane" includes a single beam or multiple beams.

As used herein, the term "Doppler" may refer to Pulsed-Wave (PW) Doppler and/or Continuous-Wave (CW) Doppler. In a preferred embodiment, the Doppler signals may be PW Doppler signals.

Furthermore, the term processor or processing unit, as used herein, refers to any type of processing unit that can carry out the required calculations needed for the various embodiments, such as single or multi-core: CPU, Accelerated Processing Unit (APU), Graphics Board, DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

FIG. 1 is a block diagram of an exemplary ultrasound system that is operable to simultaneously present Doppler signals 321-326 of a Multi-Gated Doppler (MGD) signal 320 corresponding to different anatomical structures, in accordance with various embodiments. Referring to FIG. 1, there is shown an ultrasound system 100. The ultrasound system 100 comprises a transmitter 102, an ultrasound probe 104, a transmit beamformer 110, a receiver 118, a receive beamformer 120, a RF processor 124, a RF/IQ buffer 126, a user input module 130, a signal processor 132, an image buffer 136, a display system 134, and an archive 138.

The transmitter 102 may comprise suitable logic, circuitry, interfaces and/or code that may be operable to drive an ultrasound probe 104. The ultrasound probe 104 may comprise a two dimensional (2D) array of piezoelectric elements. The ultrasound probe 104 may comprise a group of transmit transducer elements 106 and a group of receive transducer elements 108, that normally constitute the same elements. In certain embodiment, the ultrasound probe 104 may be operable to acquire ultrasound image data covering at least a substantial portion of an anatomy, such as the heart, a blood vessel, or any suitable anatomical structure.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive the signals from the receive sub-aperture beamformer 116. The analog signals may be communicated to one or more of the plurality of A/D converters 122.

The plurality of A/D converters 122 may comprise suitable logic, circuitry, interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces and/or code that may be operable to demodulate the digital signals output by the plurality of A/D converters 122. In accordance with an embodiment, the RF processor 124 may comprise a complex demodulator (not shown) that is operable to demodulate the digital signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The receive beamformer 120 may comprise suitable logic, circuitry, interfaces and/or code that may be operable to perform digital beamforming processing to, for example, sum the delayed channel signals received from RF processor 124 via the RF/IQ buffer 126 and output a beam summed signal. The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beamformer, which may be digital. In various embodiments, the ultrasound system 100 comprises a plurality of receive beamformers 120. Each of the receive beamformers 120 may be configured to perform digital beamforming to generate one of a plurality of Doppler signals that together form an MGD signal. In an exemplary embodiment, the Doppler signals of the MGD signal may be acquired simultaneously. Additionally and/or alternatively, the ultrasound system 100 may acquire different portions of the MGD signal using beam interleaving. For example, different portions of the MGD signal may be acquired based on different acquisition parameters, such as different pulse repetition frequencies or any suitable acquisition parameter. In an exemplary embodiment, beam interleaving may be executed, for example, to acquire Doppler signals of different anatomical structures using different acquisition parameters.

The user input module 130 may be utilized to input patient data, scan parameters, settings, select protocols and/or templates, select an examination type, select desired anatomical structures, select acquisition and/or display processing parameters, select a measurement type, and the like. In an exemplary embodiment, the user input module 130 may be operable to configure, manage and/or control operation of one or more components and/or modules in the ultrasound system 100. In this regard, the user input module 130 may be operable to configure, manage and/or control operation of the transmitter 102, the ultrasound probe 104, the transmit beamformer 110, the receiver 118, the receive beamformer 120, the RF processor 124, the RF/IQ buffer 126, the user input module 130, the signal processor 132, the image buffer 136, the display system 134, and/or the archive 138. The user input module 130 may include button(s), rotary encoder(s), a touchscreen, motion tracking, voice recognition, a mousing device, keyboard, camera and/or any other device capable of receiving a user directive. In certain embodiments, one or more of the user input modules 130 may be integrated into other components, such as the display system 134, for example. As an example, user input module 130 may include a touchscreen display.

In various embodiments, an examination type and/or desired anatomical structures may be selected at the onset of an imaging procedure in response to a directive received via the user input module 130. For example, an ultrasound operator may identify a diastolic dysfunction examination via the user input module 130 so that the signal processor 132 may analyze a received MGD signal to select gates corresponding with a mitral inflow signal and a tissue Doppler signal. As another example, the ultrasound operator may select the desired anatomical structure via the user input module 130 for detection by the signal processor 132 in the MGD signal. Moreover, the ultrasound operator may select, via the user input module 130, desired Doppler signal characteristics and/or combinations of characteristics for detection by the signal processor 132. Examples of Doppler signal characteristics may include highest or lowest resistive index (RI) or pulsatility index (PI) in a region, most or least spectral broadening, highest and lowest velocity (frequency shift), highest or lowest highest acceleration, highest or lowest acceleration time, highest or lowest ratio of cardiac pulsatility versus respiratory phasicity (which may help identify arterial versus venous flow), and the like. For example, the ultrasound operator may select, via the user input module 130, to identify and display the waveform with the highest velocity and most turbulence and the waveform with the highest time average peak and negative Doppler shift.

In certain embodiments, one or more measurements may be selected in response to a directive received via the user input module 130. As an example, an ultrasound operator may select an E/e' measurement via the user input module 130 so that the signal processor 132 may perform and present the measurement at the display system 132 to provide an estimated filling pressure that may be useful in diagnosing diastolic dysfunction. Examples of other measurement may include, among other things, carotid corrected flow time, velocity, time average peak, and the like. In an exemplary embodiment, acquisition parameters and/or display processing parameters for application to different anatomical structures may be identified and stored in archive 138 for retrieval by the signal processor 132 during an imaging procedure in response to a directive received via the user input module 130. For example, the ultrasound operator may select, via the user input module 130, a higher pulse repetition frequency for gates corresponding to blood flow anatomical structures and a lower pulse repetition frequency for gates corresponding to muscle tissue anatomical structures. The acquisition parameters may be stored at archive 138 or any suitable data storage medium for retrieval and application after the gates associated with the desired anatomical structures are identified. As another example, the ultrasound operator may select, via the user input module 130, a first set of display parameters for gates corresponding to blood flow anatomical structures and a second set of display parameters for gates corresponding to muscle tissue anatomical structure. The sets of display processing parameters may include scale, gain, brightness, contrast, and the like. The sets of display processing parameters may be stored at archive 138 or any suitable data storage medium for retrieval and application after the gates associated with the desired anatomical structures are identified. In a representative embodiment, MGD ultrasound data and/or a corresponding 2D image of a region of interest may be retrieved in response to a directive received via the user input module 130.

The signal processor 132 may comprise suitable logic, circuitry, interfaces and/or code that may be operable to process ultrasound scan data (i.e., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform Doppler processing, compounding, motion tracking, and/or signal processing in time and frequency domains, among other things. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), or any suitable device for storing images and related information. In the exemplary embodiment, the signal processor 132 may comprise a gate selection module 140 and a parameter application module 150.

The ultrasound system 100 may be operable to continuously acquire ultrasound scan data at a frame rate that is suitable for the imaging situation in question. Typical frame rates range from 20-70 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes' worth of frames of ultrasound scan data. The frames of ultrasound scan data are stored in a manner to facilitate retrieval thereof according to its order or time of acquisition. The image buffer 136 may be embodied as any known data storage medium.

The signal processor 132 may include a gate selection module 140 that comprises suitable logic, circuitry, interfaces and/or code that may be operable to analyze an MGD signal to automatically select gates corresponding to multiple different desired anatomical structures in a region of interest. The gate associated with each of the different desired anatomical structures may be selected by the gate selection module 140 based on one or more criterion, such as Doppler signal strength, velocity, systolic and/or diastolic flow time, resistive index (RI), pulsatility index (PI), spectral broadening (e.g., turbulent or laminar flow), acceleration, acceleration time, cardiac pulsatility versus respiratory phasicity (which may help identify arterial versus venous flow), spectrum tracking, cycle tracking, B-mode tracking, and/or combinations of the criterion. For example, the gate selection module 140 may select one of the gates based on a strongest Doppler signal strength by choosing in each sample time the gate that produces the maximal sum of absolute or squared spectrum values. As another example, the tracking module 150 may select one of the gates based on a highest velocity and/or laminar flow. In a representative embodiment, the gate selection module 140 may be configured to select the gate corresponding to the Doppler signal having the closest spectrum to a spectrum of a stored reference Doppler signal associated with a particular desired anatomical structure by applying a mean squared error or any suitable signal comparison technique. In certain embodiments, the gate selection module 140 may select the gate corresponding to one of the desired anatomical structures at a current time sample in a current heart and/or breathing cycle based on a comparison with a stored reference Doppler signal associated with the particular desired anatomical structure having a corresponding time sample in a reference heart and/or breathing cycle. In various embodiments, the gate selection module 140 may supplement the MGD signal analysis with analysis of a corresponding 2D image. The 2D ultrasound image may be a B-mode image, color Doppler image, or any suitable 2D image, being acquired by the ultrasound system 100. For example, the gate selection module 140 may select the gates corresponding to the desired anatomical structures based at least in part on analyzing a B-mode image associated with the MGD signal using image detection algorithms and techniques to identify the desired anatomical structures and corresponding gates in the B-mode image. In certain embodiments, the gate selection module 140 may apply a plurality of the above-mentioned criterion to select the gate corresponding to each of the multiple different desired anatomical structures. For example, the gate selection module 140 may weigh the spectrum tracking and the resemblance of the B-mode image frame features to select the appropriate gate corresponding to a particular desired anatomical structure in the region of interest.

Figure 3:
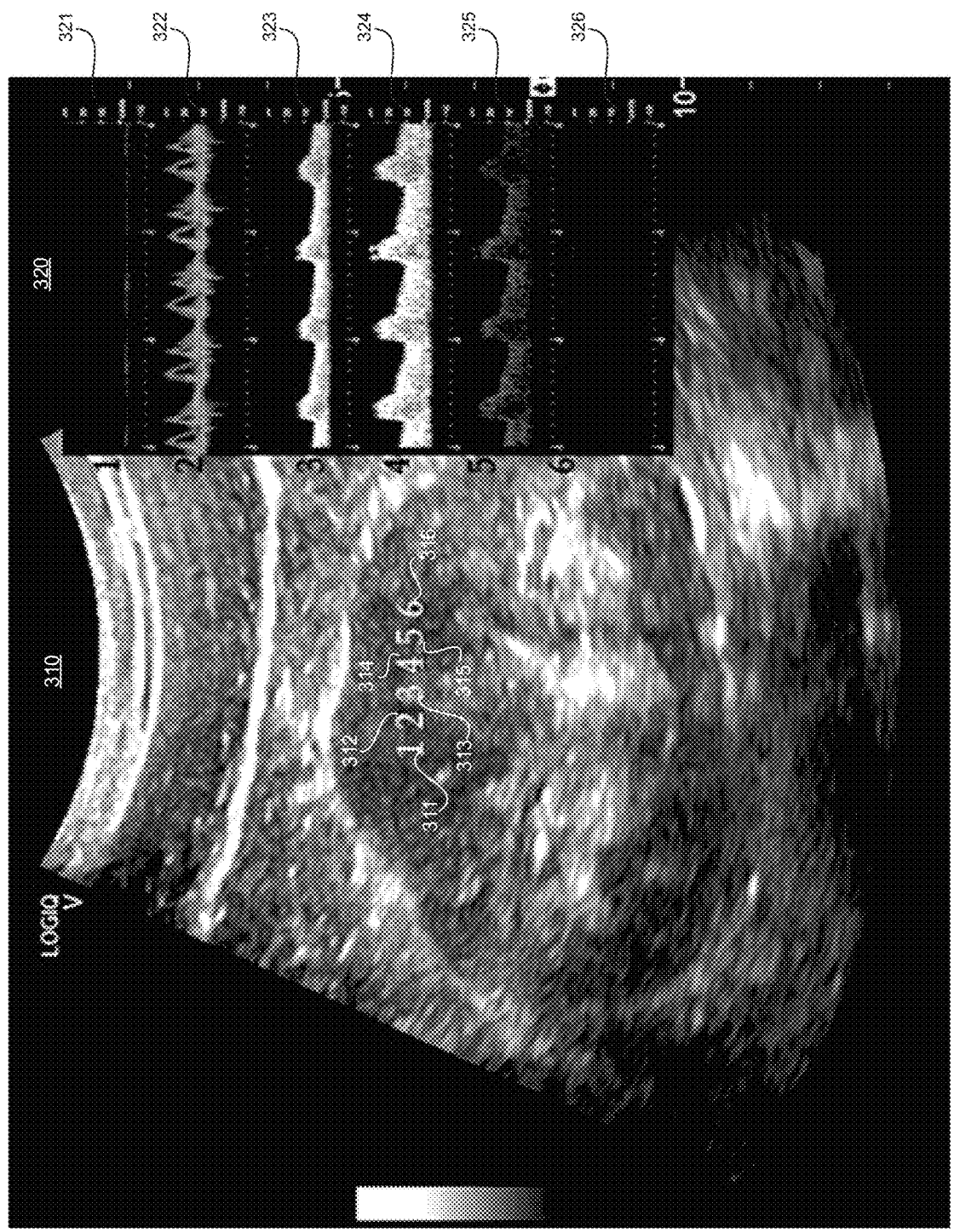
FIG. 3 illustrates an exemplary 2D image having gate locations that correspond to Doppler signals of an MGD signal, in accordance with various embodiments.

FIG. 3 illustrates an exemplary 2D image 310 having gate locations 311-316 that correspond to Doppler signals 321-326 of an MGD signal 320, in accordance with various embodiments. Referring to FIG. 3, a display system 134 may present a display 300 having a plurality of simultaneously presented Doppler signals 321-326 of an MGD signal 320. MGD allows simultaneous acquisition of Doppler signals 321-326 from many locations (i.e., gates 311-316). Each of the Doppler signals 321-326 of the MGD signal 320 may correspond with a different gate location in a region of interest. The different gate locations may correspond with different anatomical structures in the region of interest, such as blood flow, muscle tissue, and the like. In various embodiments, a 2D ultrasound image 310 may be presented with the plurality of simultaneously presented Doppler signals 321-326 of the MGD signal 320. In embodiments displaying a corresponding 2D ultrasound image 310, at least a portion of the pixels in the 2D ultrasound image 310 may correspond with different gates 311-316 of an MGD signal 320. Although 6 gates 311-316 are labeled in FIG. 3, any suitable number of gates may be implemented, such as 10 gates, 16 gates, or in a preferred embodiment, 256 gates. Each of the gates 311-316 may be associated with locations of a pixel or group of pixels in the 2D ultrasound image 310.

Referring to FIGS. 1 and 3, MGD signals 320 may be acquired with or without 2D images 310. In various embodiments, acquired MGD signals 320, and optionally 2D images 310, may be stored in archive 138 or any suitable data storage medium for retrieval and post-processing. In an exemplary embodiment, the gate selection module 140 may analyze the MGD signal 320, and optionally the 2D image 310, to detect gates 311-316 corresponding to multiple different desired anatomical structures. For example, an operator may select an examination type, anatomical structures, gate selection criterion, and/or an ultrasound measurement via a user input module 130. The operator selection may correspond with gate selection criterion for analyzing Doppler signals 321-326 of an MGD signal 320, and optionally a 2D ultrasound image 310, to detect gates corresponding to multiple different desirable anatomical structures. As an example, an operator-selected diastolic dysfunction examination type or an operator selected E/e' measurement may correspond with a first gate selection criterion for detecting a mitral inflow signal and a second gate selection criterion for detecting a tissue Doppler signal from the lateral basal segment. The gate selection module 140 retrieves the first and second gate selection criterion from archive 138 or any suitable data storage medium and applies the first and second gate selection criterion to the MGD signal 320, and optionally the 2D ultrasound image 310, to detect the gate 311-316 and associated Doppler signal 321-326 corresponding to each of the multiple different desirable anatomical structures, such as the mitral inflow signal and the tissue Doppler signal. The identification of the detected gates 311-316 and/or the associated Doppler signals 321-326 may be stored in archive 138 and/or any suitable data storage medium. The gate selection module 140 may provide the identification of the detected gates 311-316 and/or the associated Doppler signals 321-326 to the parameter application module 150 for application of acquisition and/or display processing parameters as described in more detail below.

Figure 4:
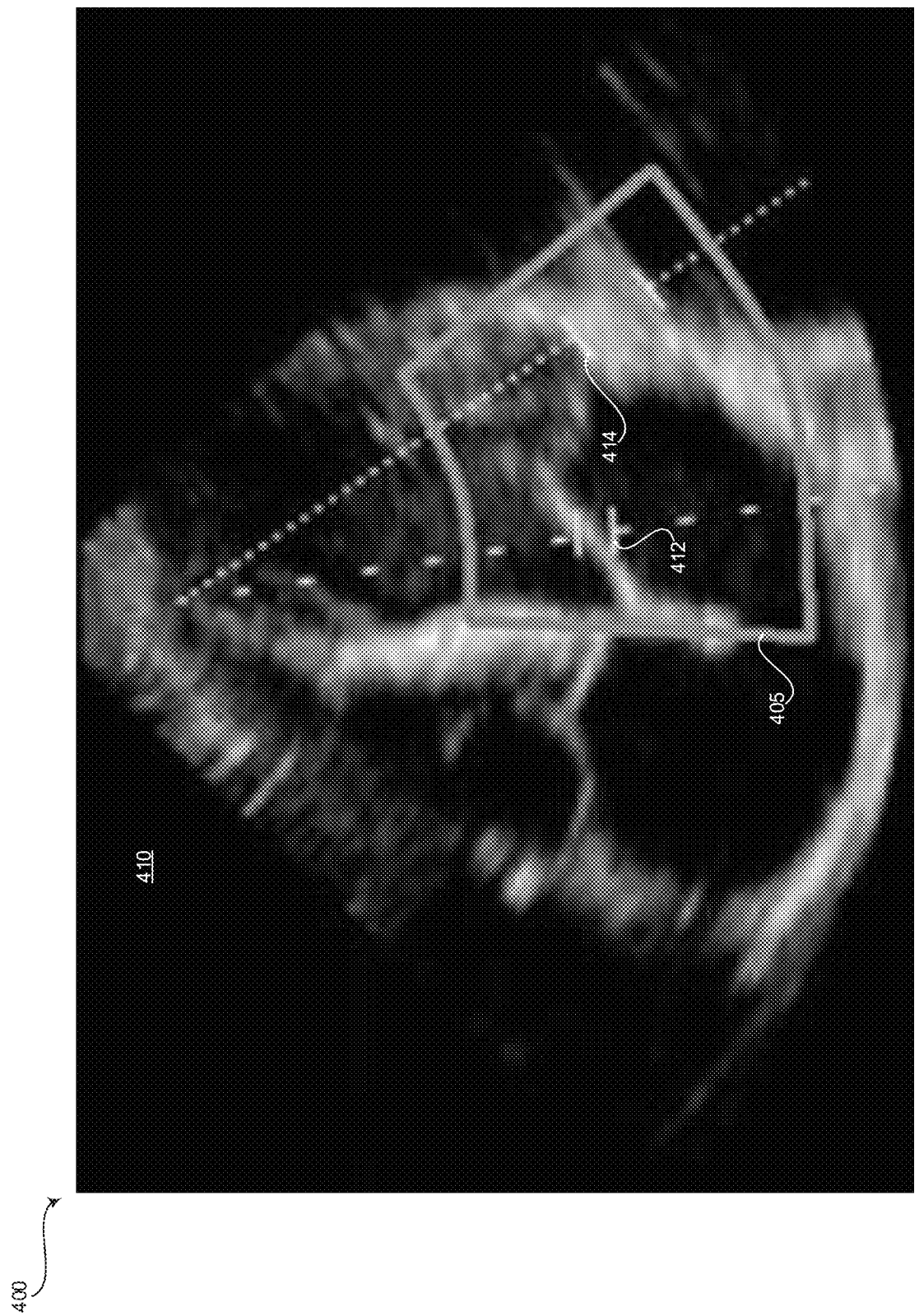
FIG. 4 illustrates an exemplary 2D image having automatically selected gate locations associated with Doppler signals of an MGD signal, in accordance with various embodiments.

FIG. 4 illustrates an exemplary 2D image 410 having automatically selected gate locations 412, 414 associated with Doppler signals of an MGD signal, in accordance with various embodiments. Referring to FIG. 4, a display system 134 may present a 2D ultrasound image 410. The 2D ultrasound image 410 may be a B-mode image, color Doppler image, or any suitable 2D image, being acquired by the ultrasound system 100. The ultrasound image 410 may include a region of interest 405 corresponding with a location where an MGD signal is acquired. The gate selection module 140 of the signal processor 132 may analyze the MGD signal to detect gate locations 412, 414 corresponding with multiple different desired anatomical structures. For example, the gate selection module 140 may select a first gate 412 associated with a Doppler signal across a mitral valve opening and a second gate 414 associated with tissue Doppler of the mitral valve annulus to perform an E/e' ratio measurement (i.e., the ratio of mitral peak velocity of early filling (E) to early diastolic mitral annular velocity (e')) and/or to simultaneously present the Doppler signals corresponding to the gate locations 412, 414 at a display system 134.

Referring again to FIG. 1, the signal processor 132 may include a parameter application module 150 that comprises suitable logic, circuitry, interfaces and/or code that may be operable to apply image acquisition parameters and/or display processing parameters in response to the selection of the gates 311-316, 412, 414 associated with Doppler signals 321-326 corresponding to the multiple different desired anatomical structures by the gate selection module 140. For example, the parameter application module 150 may be configured to receive sets of image acquisition parameters corresponding to each of the selected gates 311-316, 412, 414. The image acquisition parameters may be received from an ultrasound operator via the user input module 130 and/or may be retrieved from archive 138 or any suitable data storage medium. The parameter application module 150 may control the ultrasound system 100 to acquire an MGD signal 320 having Doppler signals 321-326 corresponding to the selected gates 311-316 based on the image acquisition parameters. The Doppler signals 321-326 corresponding to the selected gates 311-316, 412, 414 may be acquired by applying the different sets of image acquisition parameters. As an example, the parameter application module 150 may control the ultrasound system 100 to acquire a Doppler signal of a first selected gate 412 associated with a mitral valve opening based on a first set of image acquisition parameters and may control the ultrasound system 100 to acquire a Doppler signal of a second selected gate 414 associated with the mitral valve annulus based on a second set of image acquisition parameters. The first and second sets of image acquisition parameters may include different values associated with the parameters. For example, the first set of image acquisition parameters may define a first, higher pulse repetition frequency (PRF) for acquisition of ultrasound data corresponding to blood flow and the second set of image acquisition parameters may define a second, lower PRF for acquisition of ultrasound data corresponding to muscle tissue. In various embodiments, the MGD signal 320 may be acquired by performing beam interleaving. For example, the ultrasound system 100 may alternate between transmitting four ultrasound pulses at the first selected gate 412 associated with the blood flow anatomical structure and one ultrasound pulse at the second selected gate 414 associated with the muscle tissue anatomical structure. The image acquisition parameters may include PRF, depth, intensity, and/or any suitable image acquisition parameters. Each of the Doppler signals 321-326 of the MGD signal 320 acquired based on the appropriate set of image acquisition parameters may be simultaneously presented at the display system 134 and/or processed by the parameter application module 150.

As another example, the parameter application module 150 may comprise suitable logic, circuitry, interfaces and/or code that may be operable to apply display processing parameters in response to the selection of the gates 311-316, 412, 414 associated with Doppler signals 321-326 corresponding to the multiple different desired anatomical structures by the gate selection module 140. For example, the parameter application module 150 may be configured to receive sets of display processing parameters corresponding to each of the selected gates 311-316, 412, 414. The display processing parameters may be received from an ultrasound operator via the user input module 130 and/or may be retrieved from archive 138 or any suitable data storage medium. The parameter application module 150 may process each of the Doppler signals 321-326 associated with each of the selected gates 311-316, 412, 414 by applying the appropriate set of display processing parameters. In various embodiments, each set of display processing parameters may be configured to enhance visualization of the corresponding Doppler signal 321-326 based on the associated anatomical structure. For example, a first set of display processing parameters may be optimized for displaying a Doppler signal of a blood flow anatomical structure and a different second set of display processing parameters may be optimized for displaying a Doppler signal of a muscle tissue anatomical structure. As another example, a first set of display processing parameters may be optimized for displaying a Doppler signal of a venous blood flow anatomical structure and a different second set of display processing parameters may be optimized for displaying a Doppler signal of an arterial blood flow anatomical structure. The display processing parameters may include scale, brightness, gain, contrast, and/or any suitable display processing parameter. In a representative embodiment, each of the Doppler signals 321-326 of the MGD signal 320 selected by the gate selection module 140 and processed by the parameter application module 150 based on the appropriate set of display processing parameters is simultaneously presented at the display system 134.

Still referring to FIG. 1, the signal processor 132 may comprise suitable logic, circuitry, interfaces and/or code that may be operable to automatically perform measurements on the simultaneously displayed Doppler signals 321-326 of the MGD signal 320 selected by the gate selection module 140 and acquired and/or processed by the parameter application module 150 based on the appropriate set of image acquisition and/or display processing parameters. For example, the signal processor 132 may receive a selected examination type, anatomical structures, gate selection criterion, and/or an ultrasound measurement. The selection may be received by the signal processor 132 via a user input module 130 and/or by the signal processor 132 retrieving stored or default setting from archive 138 and/or any suitable data storage medium. The selection may identify and/or correspond with one or more measurements. The measurements may include an E/e' ratio, carotid corrected flow time, velocity, time average peak, and/or any suitable measurement. For example, a selection of a diastolic dysfunction examination may correspond with an E/e' ratio measurement that may be automatically performed by the signal processor 132 and presented with the simultaneous display of the Doppler signals 321-326 at the display system 134.

Figure 2:
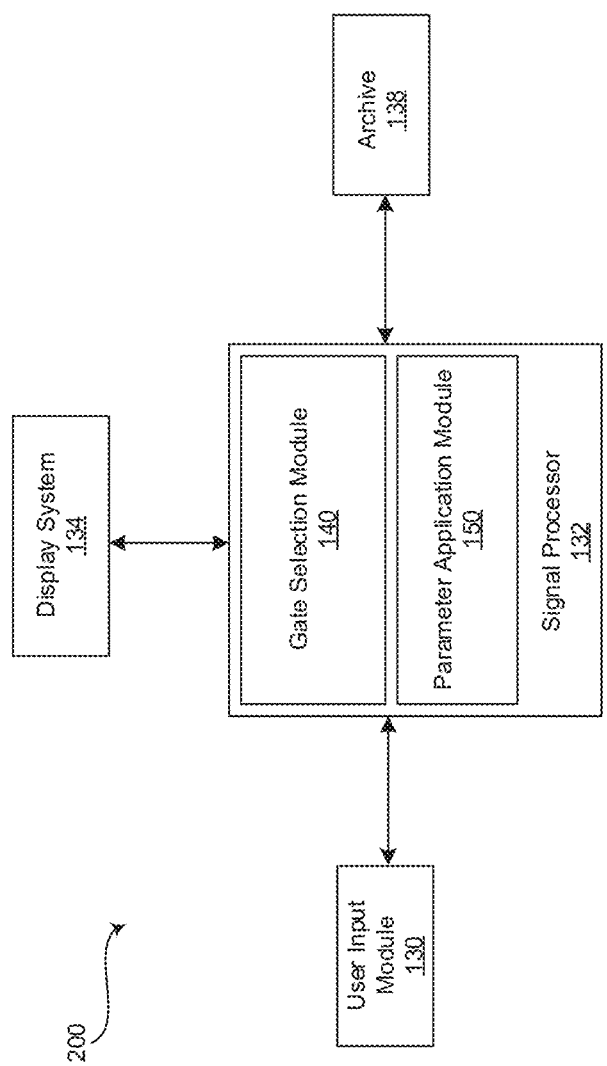
FIG. 2 is a block diagram of an exemplary medical workstation that is operable to simultaneously present Doppler signals of an MGD signal corresponding to different anatomical structures, in accordance with various embodiments.

FIG. 2 is a block diagram of an exemplary medical workstation 200 that is operable to simultaneously present Doppler signals 321-326 of an MGD signal 320 corresponding to different anatomical structures, in accordance with various embodiments. In various embodiments, components of the medical workstation 200 may share various characteristics with components of the ultrasound system 100, as illustrated in FIG. 1 and described above. Referring to FIG. 2, the medical workstation 200 comprises a display system 134, a signal processor 132, an archive 138, and a user input module 130, among other things. Components of the medical workstation 200 may be implemented in software, hardware, firmware, and/or the like. The various components of the medical workstation 200 may be communicatively linked. Components of the medical workstation 200 may be implemented separately and/or integrated in various forms.

For example, the display system 134 and the user input module 130 may be integrated as a touchscreen display.

The display system 134 may be any device capable of communicating visual information to a user. For example, a display system 134 may include a liquid crystal display, a light emitting diode display, and/or any suitable display or displays. The display system 134 can be operable to display information from the signal processor 132 and/or archive 138, such as B-mode images 310, 410, color Doppler images, Doppler signals 321-326, ultrasound measurements, and/or any suitable information. In various embodiments, the display system 134 is operable to simultaneously present at least two Doppler signals 321-326 corresponding to different selected anatomical structures acquired and/or processed based on different sets of acquisition and/or display processing parameters.

The signal processor 132 may be one or more central processing units, microprocessors, microcontrollers, and/or the like. The signal processor 132 may be an integrated component, or may be distributed across various locations, for example. The signal processor 132 comprises a gate selection module 140 and a parameter application module 150, as described above with reference to FIG. 1, and may be capable of receiving input information from a user input module 130 and/or archive 138, generating an output displayable by a display system 134, and manipulating the output in response to input information from a user input module 130, among other things. The signal processor 132, gate selection module 140, and/or parameter application module 150 may be capable of executing any of the method(s) and/or set(s) of instructions discussed herein in accordance with the various embodiments, for example.

The archive 138 may be one or more computer-readable memories integrated with the medical workstation 200 and/or communicatively coupled (e.g., over a network) to the medical workstation 200, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things. In various embodiments, the archive 138 stores medical image data, image acquisition parameters, display processing parameters, instructions for analyzing an MGD signal 320 to automatically select gates 311-316, 412, 414 corresponding to multiple different desired anatomical structures in a region of interest 405, instructions for applying image acquisition parameters and/or display processing parameters to Doppler signals 321-326 in response to the selection of the gates 311-316, 412, 414, and simultaneously presenting the Doppler signals 321-326 corresponding to different selected anatomical structures acquired and/or processed based on different sets of acquisition and/or display processing parameters, for example.

The user input module 130 may include any device(s) capable of communicating information from a user and/or at the direction of the user to the signal processor 132 of the medical workstation 200, for example. As discussed above with respect to FIG. 1, the user input module 130 may include a touch panel, button(s), a mousing device, keyboard, rotary encoder, trackball, camera, voice recognition, and/or any other device capable of receiving a user directive.

Figure 5:
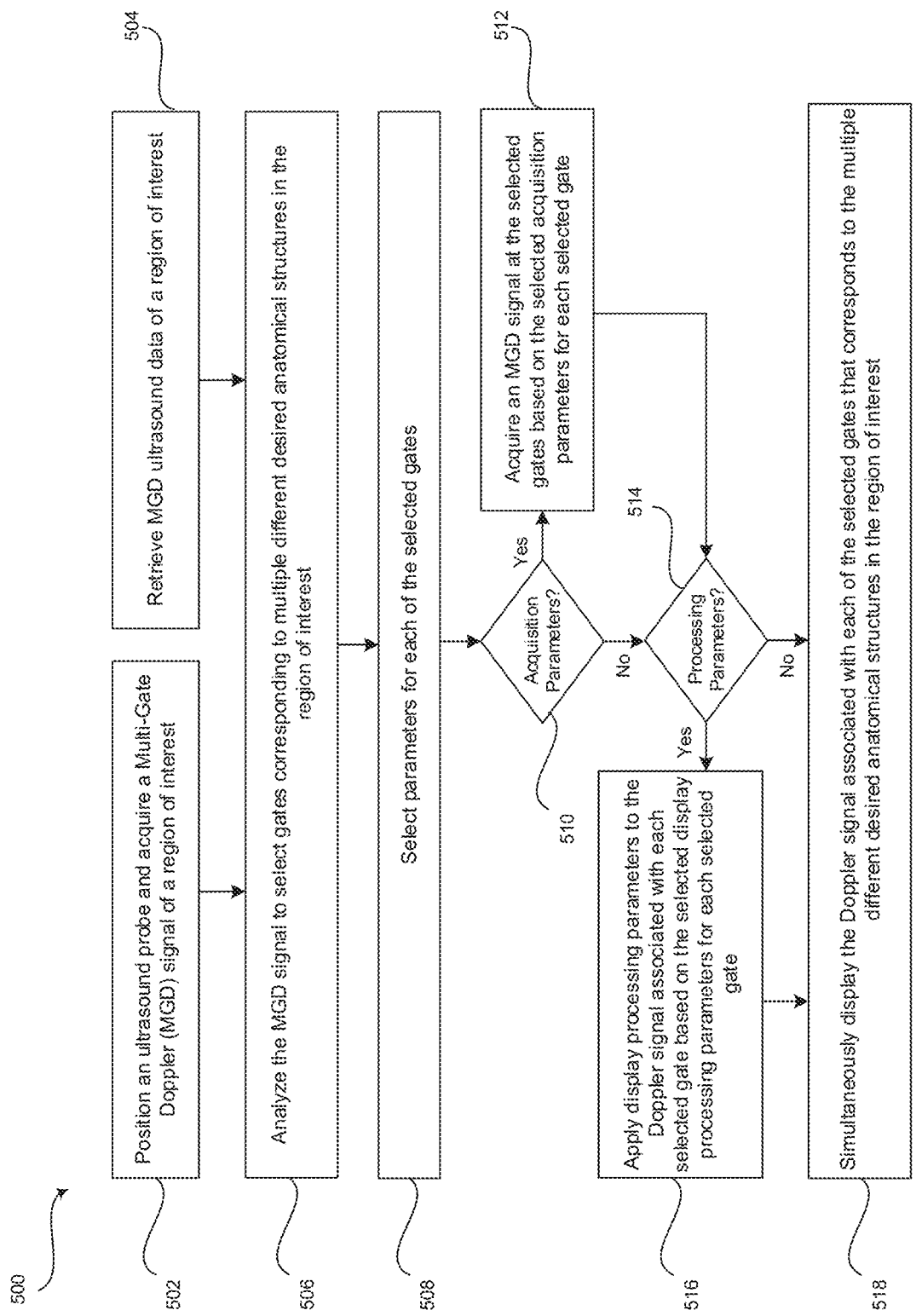
FIG. 5 is a flow chart illustrating exemplary steps that may be utilized for simultaneously presenting Doppler signals of an MGD signal corresponding to different anatomical structures, in accordance with exemplary embodiments.

FIG. 5 is a flow chart 500 illustrating exemplary steps 502-518 that may be utilized for simultaneously presenting Doppler signals 321-326 of an MGD signal 320 corresponding to different anatomical structures, in accordance with exemplary embodiments. Referring to FIG. 5, there is shown a flow chart 500 comprising exemplary steps 502 through 518. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 502, a probe 104 of an ultrasound system 100 may be positioned to acquire a MGD signal 320 of a region of interest 405. For example, the ultrasound system 100 may acquire the MGD signal 320 with an ultrasound probe 104 positioned over a region of interest 405, such as venous blood flow, arterial blood flow, mitral inflow, muscle tissue, and/or any suitable anatomical structures. In various embodiments, the probe 104 may be operable to acquire 2D ultrasound image data 310, 410 corresponding to the MGD signal 320.

At step 504, a signal processor 132 may retrieve MGD ultrasound data 320 of a region of interest 405. For example, the signal processor 132 of a workstation 200 or ultrasound system 100 may retrieve the MGD ultrasound data 320 from an archive 138 or any suitable data storage medium. In various embodiments, the signal processor 132 may retrieve 2D images 310, 410 corresponding to the MGD ultrasound data 320.

At step 506, the signal processor 132 of the ultrasound system 100 may analyze the MGD signal 320 to select gates 311-316, 412, 414 corresponding to multiple different desired anatomical structures in the region of interest 405. For example, a gate selection module 140 of the signal processor 132 may analyze the MGD signal 320, and optionally the 2D image 310, to detect gates 311-316, 414, 416 corresponding to multiple different desired anatomical structures. In various embodiments, the desired anatomical structures may be specified by an ultrasound operator or other medical professional. For example, the operator may select an examination type, anatomical structures, gate selection criterion, and/or an ultrasound measurement via a user input module 130. The operator selection may correspond with multiple desired anatomical structures. The operator selection may be associated with gate selection criterion for analyzing Doppler signals 321-326 of an MGD signal 320, and optionally a 2D ultrasound image 310, to detect gates 311-316, 412, 414 corresponding to the multiple different desirable anatomical structures. The gate selection criterion may include various Doppler characteristics, and optionally 2D image characteristics, such as Doppler signal strength, velocity, resistive index (RI), pulsatility index (PI), spectral broadening (e.g., turbulent or laminar flow), acceleration, acceleration time, cardiac pulsatility versus respiratory phasicity, spectrum tracking, cycle tracking, B-mode tracking, and/or combinations of the criterion. The gate selection module 140 retrieves the gate selection criterion corresponding to each of the desired anatomical structures from archive 138 or any suitable data storage medium and applies each of the gate selection criterion to the MGD signal 320, and optionally the 2D ultrasound image 310, to detect the gate 311-316 and associated Doppler signal 321-326 corresponding to each of the multiple different desirable anatomical structures. The identification of the detected gates 311-316 and/or the associated Doppler signals 321-326 may be stored in archive 138 and/or any suitable data storage medium. The detected gates 311-316, 412, 414 and/or the associated Doppler signals 321-326 identified by the gate selection module 140 may be provided to the parameter application module 150 of the signal processor 132.

At step 508, the signal processor 132 may select parameters for each of the selected gates 311-316, 412, 414. For example, a parameter application module 150 of the signal processor 132 may receive the detected gates 311-316, 412, 414 and/or the associated Doppler signals 321-326 from archive 138 and/or the gate selection module 140. The parameter application module 150 may select the appropriate set of image acquisition parameters and/or display processing parameters based on the anatomical structure associated with each of the detected gates 311-316, 412, 414 and/or the associated Doppler signals 321-326. The parameter application module 150 may be configured to receive the selected sets of image acquisition parameters and/or display processing parameters corresponding to each of the selected gates 311-316, 412, 414 from an ultrasound operator via the user input module 130 and/or from archive 138 or any suitable data storage medium. The image acquisition parameters may include PRF, depth, intensity, and/or any suitable image acquisition parameters. The display processing parameters may include brightness, gain, contrast, and/or any suitable display processing parameter. Each of the sets of image acquisition parameters and/or display processing parameters may be defined to provide enhanced visualization of the Doppler signal 321-326 corresponding to the particular anatomical structure to which the set of parameters is associated.

At step 510, the signal processor 132 determines whether the selected parameters are image acquisition parameters. For example, if the parameter application module 150 receives image acquisition parameters corresponding to each of the selected gates 311-316, 412, 414, the process proceeds to step 512. If the parameter application module 150 does not receive image acquisition parameters corresponding to each of the selected gates 311-316, 412, 414, the process proceeds to step 514.

At step 512, the ultrasound system 100 may acquire an MGD signal 320 at the selected gates 311-316, 412, 414 based on the selected image acquisition parameters for each of the selected gates 311-316, 412, 414. For example, the parameter application module 150 of the signal processor 132 may control the ultrasound system 100 to acquire the MGD signal 320 having Doppler signals 321-326 corresponding to the selected gates 311-316 based on the image acquisition parameters selected at step 508. The Doppler signals 321-326 corresponding to the selected gates 311-316, 412, 414 are acquired by applying the different sets of image acquisition parameters. The different sets of image acquisition parameters may include at least some different values associated with the parameters. In various embodiments, the MGD signal 320 may be acquired by performing beam interleaving.

At step 514, the signal processor 132 determines whether the selected parameters are display processing parameters. For example, if the parameter application module 150 receives display processing parameters corresponding to each of the selected gates 311-316, 412, 414, the process proceeds to step 516. If the parameter application module 150 does not receive display processing parameters corresponding to each of the selected gates 311-316, 412, 414, the process proceeds to step 518.

At step 516, the signal processor 132 may apply display processing parameters to the Doppler signals 321-326 associated with each selected gate 311-316, 412, 414 based on the selected display processing parameters for each selected gate 311-316, 412, 414. For example, the parameter application module 150 of the signal processor 132 may process each of the Doppler signals 321-326 associated with each of the selected gates 311-316, 412, 414 by applying the appropriate set of display processing parameters selected at step 508. In various embodiments, each set of display processing parameters may be configured to enhance visualization of the corresponding Doppler signal 321-326 based on the associated anatomical structure.

At step 518, the signal processor 132 may simultaneously display the Doppler signals 321-326 associated with each of the selected gate 311-316 that corresponds to the multiple different desired anatomical structures in the region of interest 405. For example, the parameter application module 150 of the signal processor 132 may present each of the Doppler signals 321-326 simultaneously at a display system 134 of the ultrasound system 100 and/or workstation 200. In various embodiments, the Doppler signals 321-326 may be presented with 2D ultrasound image data 310, 410 and/or measurements performed by the signal processor 132. For example, the signal processor 132 may be operable to automatically perform measurements on the simultaneously displayed Doppler signals 321-326 of the MGD signal 320 selected by the gate selection module 140 and acquired and/or processed by the parameter application module 150 based on the appropriate set of image acquisition and/or display processing parameters. The measurements may include an E/e' ratio, carotid corrected flow time, velocity, time average peak, and/or any suitable measurement. The measurements performed may correspond with an operator-selected examination type, anatomical structures, gate selection criterion, and/or ultrasound measurement.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set $\{(x), (y), (x, y)\}$. As another example, "x, y, and/or z" means any element of the seven-element set $\{(x), (y), (z), (x, y), (x, z), (y, z), (x, y, z)\}$. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for simultaneously presenting Doppler signals of a Multi-Gated Doppler (MGD) signal corresponding to different anatomical structures.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method comprising:
analyzing, by at least one processor, a Multi-Gated Doppler (MGD) signal of a region of interest to select multiple gates from a plurality of gates, the MGD signal comprising a plurality of Doppler signals, each of the plurality of gates corresponding with one of the plurality of Doppler signals, and each of the selected multiple gates associated with one of a plurality of different anatomical structures in the region of interest;
selecting, by the at least one processor, one of a plurality of sets of parameters for each of the selected multiple gates;
applying, by the at least one processor, each of the selected one of the plurality of sets of parameters for each of the selected multiple gates; and
simultaneously presenting, at a display system, the one of the plurality of Doppler signals for each of the selected multiple gates after the each of the selected one of the plurality of sets of parameters is applied.

2. The method of claim 1, comprising receiving, by the at least one processor, the MGD signal from one or both of an ultrasound probe or a data storage medium.

3. The method of claim 1, wherein each of the selected multiple gates is selected by the at least one processor based on different one or more criterion.

4. The method of claim 3, wherein the different one or more criterion comprises at least one of:
Doppler signal strength,
velocity,
resistive index,
pulsatility index,
systolic flow time,
diastolic flow time,
acceleration,
acceleration time,
cardiac pulsatility versus respiratory phasicity,
spectral broadening, and
two-dimensional (2D) image analysis of a 2D ultrasound image corresponding to the MGD signal.

5. The method of claim 1, wherein:
the selected one of the plurality of sets of parameters for each of the selected multiple gates is a different set of image acquisition parameters comprising a different value associated with pulse repetition frequency, and
the applying each of the selected one of the plurality of sets of parameters comprises acquiring an MGD signal at the selected multiple gates based on the different set of image acquisition parameters using beam interleaving.

6. The method of claim 1, wherein the selected one of the plurality of sets of parameters for each of the selected multiple gates is a different set of display processing parameters.

7. The method of claim 6, wherein each of the different set of display processing parameters comprises at least one of:
scale,
gain,
brightness, and
contrast.

8. The method of claim 1, comprising presenting, at the display system, at least one ultrasound measurement automatically performed by the at least one processor.

9. A system comprising:
at least one processor configured to:
analyze a Multi-Gated Doppler (MGD) signal of a region of interest to select multiple gates from a plurality of gates, the MGD signal comprising a plurality of Doppler signals, each of the plurality of gates corresponding with one of the plurality of Doppler signals, and each of the selected multiple gates associated with one of a plurality of different anatomical structures in the region of interest;
select one of a plurality of sets of parameters for each of the selected multiple gates; and
apply each of the selected one of the plurality of sets of parameters for each of the selected multiple gates; and
a display system configured to simultaneously present the one of the plurality of Doppler signals for each of the selected multiple gates after the each of the selected one of the plurality of sets of parameters is applied.

10. The system of claim 9, comprising one or both of:
an ultrasound probe configured to provide the MGD signal to the at least one processor, and
a data storage medium configured to provide the MGD signal to the at least one processor.

11. The system of claim 9, wherein each of the selected multiple gates is selected by the at least one processor based on different one or more criterion.

12. The system of claim 11, wherein the different one or more criterion comprises at least one of:
Doppler signal strength,
velocity,
resistive index,
pulsatility index,
systolic flow time, diastolic flow time,
acceleration,
acceleration time,
cardiac pulsatility versus respiratory phasicity,
spectral broadening, and
two-dimensional (2D) image analysis of a 2D ultrasound image corresponding to the MGD signal.

13. The system of claim 9, wherein:
the selected one of the plurality of sets of parameters for each of the selected multiple gates is a different set of image acquisition parameters comprising a different value associated with pulse repetition frequency, and
each of the selected one of the plurality of sets of parameters is applied by acquiring an MGD signal at the selected multiple gates based on the different set of image acquisition parameters using beam interleaving.

14. The system of claim 9, wherein:
the selected one of the plurality of sets of parameters for each of the selected multiple gates is a different set of display processing parameters, and
each of the different set of display processing parameters comprises at least one of:
scale,
gain,
brightness, and
contrast.

15. The system of claim 9, wherein the at least one processor is configured to automatically perform at least one ultrasound measurement for presentation at the display system.

16. A non-transitory computer readable medium having stored thereon, a computer program having at least one code section, the at least one code section being executable by a machine for causing the machine to perform steps comprising:
analyzing a Multi-Gated Doppler (MGD) signal of a region of interest to select multiple gates from a plurality of gates, the MGD signal comprising a plurality of Doppler signals, each of the plurality of gates corresponding with one of the plurality of Doppler signals, and each of the selected multiple gates associated with one of a plurality of different anatomical structures in the region of interest;
selecting one of a plurality of sets of parameters for each of the selected multiple gates;
applying each of the selected one of the plurality of sets of parameters for each of the selected multiple gates; and
simultaneously presenting the one of the plurality of Doppler signals for each of the selected multiple gates at a display system after the each of the selected one of the plurality of sets of parameters is applied.

17. The non-transitory computer readable medium of claim 16, wherein each of the selected multiple gates is selected based on different one or more criterion comprising at least one of:
Doppler signal strength,
velocity,
resistive index,
pulsatility index,
systolic flow time,
diastolic flow time,
acceleration,
acceleration time,
cardiac pulsatility versus respiratory phasicity,
spectral broadening, and
two-dimensional (2D) image analysis of a 2D ultrasound image corresponding to the MGD signal.

18. The non-transitory computer readable medium of claim 16, wherein:
the selected one of the plurality of sets of parameters for each of the selected multiple gates is a different set of image acquisition parameters comprising a different value associated with pulse repetition frequency, and
each of the selected one of the plurality of sets of parameters is applied by acquiring an MGD signal at the selected multiple gates based on the different set of image acquisition parameters using beam interleaving.

19. The non-transitory computer readable medium of claim 16, wherein:
the selected one of the plurality of sets of parameters for each of the selected multiple gates is a different set of display processing parameters, and
each of the different set of display processing parameters comprises at least one of:
scale,
gain,
brightness, and
contrast.

20. The non-transitory computer readable medium of claim 16, comprising automatically performing at least one ultrasound measurement and presenting the at least one ultrasound measurement at the display system.

* * * * *